(12) United States Patent
Wolf et al.

(10) Patent No.: US 10,538,470 B2
(45) Date of Patent: *Jan. 21, 2020

(54) PROCESS FOR THE PREPARATION OF LIMONENE-4-OL

(71) Applicant: BASF Agro B.V., Arnhem (NL)

(72) Inventors: Bernd Wolf, Niederkirchen (DE);
Michael Rack, Eppelheim (DE); Stefan Benson, Bensheim (DE); Helmut Kraus, Wissembourg (FR); Roland Goetz, Neulussheim (DE); Sukunath Narayanan, Mumbai (IN); Chidambaram Rishinaradamangalam, Hosur (IN)

(73) Assignee: BASF Agro B.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/571,987

(22) PCT Filed: Apr. 22, 2016

(86) PCT No.: PCT/EP2016/058963
§ 371 (c)(1),
(2) Date: Nov. 6, 2017

(87) PCT Pub. No.: WO2016/180614
PCT Pub. Date: Nov. 17, 2016

(65) Prior Publication Data
US 2018/0134641 A1    May 17, 2018

(30) Foreign Application Priority Data

May 8, 2015 (IN) .......................... 1291/DEL/2015
Jun. 30, 2015 (EP) .................................... 15174608

(51) Int. Cl.
C07D 307/00 (2006.01)
C07C 29/56 (2006.01)
C07C 29/17 (2006.01)
C07D 493/08 (2006.01)

(52) U.S. Cl.
CPC .............. *C07C 29/56* (2013.01); *C07C 29/17* (2013.01); *C07D 493/08* (2013.01); *C07C 2601/16* (2017.05)

(58) Field of Classification Search
CPC ..... C07C 29/56; C07C 29/17; C07C 2601/16; C07D 493/08
USPC .......................................................... 549/463
See application file for complete search history.

(56) References Cited

U.S. PATENT DOCUMENTS

| 3,676,504 A * | 7/1972 | Leffingwell ............ C07C 35/18 568/825 |
| 4,257,948 A | 3/1981 | Costerousse et al. |
| 4,487,945 A | 12/1984 | Payne |
| 4,542,244 A | 9/1985 | Payne et al. |
| 4,898,954 A | 2/1990 | Mohrmann |
| 4,945,100 A | 7/1990 | Nyfeler |
| 4,992,458 A | 2/1991 | Riebli |
| 5,143,932 A | 9/1992 | Jautelat |
| 2017/0305849 A1 | 10/2017 | Schaefer et al. |
| 2018/0141924 A1* | 5/2018 | Wolf ...................... C07C 29/17 |

FOREIGN PATENT DOCUMENTS

| CA | 1171866 A1 | 7/1984 |
| CA | 1209152 A1 | 8/1986 |
| CN | 1467029 | 1/2004 |
| CN | 101602770 | 12/2009 |
| DE | 3042302 A1 | 8/1981 |
| DE | 3315681 A1 | 10/1984 |
| DE | 3733755 A1 | 4/1989 |
| DE | 4003180 A1 | 8/1991 |
| EP | 0081893 | 6/1983 |
| EP | 0113640 A2 | 7/1984 |
| EP | 0126430 A2 | 11/1984 |
| EP | 0275955 A1 | 7/1988 |
| EP | 0298020 | 1/1989 |
| EP | 0081893 | 6/1993 |
| EP | 0735142 A2 | 10/1996 |
| GB | 1307053 * | 2/1973 |
| JP | H0248541 | 2/1990 |
| WO | 02085891 A1 | 10/2002 |
| WO | 2006128126 | 11/2006 |
| WO | 13007767 A1 | 1/2013 |
| WO | 13010862 A1 | 1/2013 |
| WO | 13066360 A1 | 5/2013 |
| WO | 13124791 A1 | 8/2013 |
| WO | 13189910 A1 | 12/2013 |
| WO | 14012811 A1 | 1/2014 |
| WO | 14026845 A1 | 2/2014 |
| WO | 14026893 A1 | 2/2014 |
| WO | 14026928 A1 | 2/2014 |
| WO | 14060449 A1 | 4/2014 |
| WO | 14108286 A1 | 7/2014 |
| WO | 14111398 A1 | 7/2014 |

(Continued)

OTHER PUBLICATIONS

Aldrich (Handbook of Fine Chemicals: Aldrich,1998-1999, p. 637, and 1645-1646(4 pages) (Year: 1998).*
Extended European Search Report, issued in corresponding Application No. 15174608.8, dated Oct. 6, 2015.
Gurudutt et al., "Acid-Catalysed Rearrangement of Terpinolene Oxide," Indian Journal of Chemistry, Section B, Council of Scientific and Industrial Research, vol. 24B, (1985), pp. 820-823.
International Search Report, issued in PCT/EP2016/058963, dated Jun. 29, 2016.
The Pesticide Manual, 14th Ed., C.D.S. Tomlin, British Crop Production Council, Entry 157, (2006), pp. 195-196.

(Continued)

*Primary Examiner* — Taylor V Oh
(74) *Attorney, Agent, or Firm* — Brinks Gilson & Lione

(57) ABSTRACT

The present invention relates to a process for the preparation of limonene-4-ol by an epoxide ring opening isomerization of terpinolene epoxide.

19 Claims, No Drawings

(56) References Cited

FOREIGN PATENT DOCUMENTS

| | | |
|---|---|---|
| WO | 2014108286 | 7/2014 |
| WO | 14135392 A1 | 9/2014 |
| WO | 14155214 A1 | 10/2014 |
| WO | 2014184014 | 11/2014 |
| WO | 2014184015 | 11/2014 |
| WO | 2014184016 | 11/2014 |
| WO | 2014184017 | 11/2014 |
| WO | 2014184019 | 11/2014 |
| WO | 2014184073 | 11/2014 |
| WO | 2014184074 | 11/2014 |
| WO | 2014187705 | 11/2014 |
| WO | 14202589 A1 | 12/2014 |
| WO | 2014202589 | 12/2014 |
| WO | 15011119 A2 | 1/2015 |
| WO | 15011120 A2 | 1/2015 |
| WO | 2015003858 | 1/2015 |
| WO | 2015007564 | 1/2015 |
| WO | 2015022634 | 2/2015 |
| WO | 15055447 A1 | 4/2015 |
| WO | 2015049160 | 4/2015 |
| WO | 2015049360 | 4/2015 |
| WO | 2015052152 | 4/2015 |
| WO | 2015052153 | 4/2015 |
| WO | 2015052173 | 4/2015 |
| WO | 2015052178 | 4/2015 |
| WO | 2015055447 | 4/2015 |
| WO | 2015067494 | 5/2015 |
| WO | 2015075087 | 5/2015 |
| WO | 15086596 A1 | 6/2015 |
| WO | 15091045 A1 | 6/2015 |
| WO | 2015082415 | 6/2015 |
| WO | 2015082422 | 6/2015 |
| WO | 2015086698 | 6/2015 |
| WO | 2015091045 | 6/2015 |
| WO | 2015124651 | 8/2015 |
| WO | 15158518 A1 | 10/2015 |
| WO | 2015155236 | 10/2015 |
| WO | 2015158518 | 10/2015 |
| WO | 2015158565 | 10/2015 |
| WO | 15169883 A1 | 11/2015 |
| WO | 16001025 A1 | 1/2016 |
| WO | 2016005211 | 1/2016 |
| WO | 2016016369 | 1/2016 |
| WO | 2016037785 | 3/2016 |
| WO | 2016055404 | 4/2016 |
| WO | 2016062814 | 4/2016 |
| WO | 2016071243 | 5/2016 |
| WO | 2016180642 | 11/2016 |
| WO | 2016180833 | 11/2016 |
| WO | 2016202807 | 12/2016 |
| WO | WO17009054 A1 | 1/2017 |
| WO | WO17009056 A1 | 1/2017 |
| WO | WO17009060 A1 | 1/2017 |
| WO | WO17009061 A1 | 1/2017 |
| WO | WO17009088 A1 | 1/2017 |
| WO | WO17009089 A1 | 1/2017 |
| WO | WO17009090 A1 | 1/2017 |
| WO | WO17009092 A1 | 1/2017 |
| WO | WO17009095 A1 | 1/2017 |
| WO | WO17009124 A1 | 1/2017 |
| WO | WO17009134 A1 | 1/2017 |
| WO | WO17009137 A1 | 1/2017 |
| WO | WO17009138 A1 | 1/2017 |
| WO | WO17009139 A1 | 1/2017 |
| WO | WO17009140 A1 | 1/2017 |
| WO | WO17009142 A1 | 1/2017 |
| WO | WO17009143 A1 | 1/2017 |
| WO | WO17009144 A1 | 1/2017 |
| WO | WO17009145 A1 | 1/2017 |
| WO | WO17009146 A1 | 1/2017 |
| WO | WO17009147 A1 | 1/2017 |
| WO | WO17009148 A1 | 1/2017 |
| WO | WO17012938 A1 | 1/2017 |
| WO | WO17102905 A1 | 6/2017 |
| WO | WO17133942 A1 | 8/2017 |

OTHER PUBLICATIONS

International Preliminary Report on Patentability, issued in PCT/EP2016/058963, dated May 23, 2017.
Brandes and Jacobsen, "Synthesis of Enantiopure 3-chlorostyrene Oxide via an Asymmetric Epoxidation-Hydrolytic Kinetic Resolution Sequence," Tetrahedron:Asymmetry, vol. 8, No. 23, (1997), pp. 3927-3933.
Forrester et al., "Generation of Trimethylsulfonium Cation from Dimethyl Sulfoxide and Dimethyl Sulfate: Implications for the Synthesis of Epoxides from Aldehydes and Ketones," J. Chem. Soc. Perkin Trans. (1995), pp. 2289-2291.
Kuzenkov, "Synthesis of Substituted 2-azolyl-1-pyridylethan-1-ols," Chemistry of Heterocyclic Compounds, vol. 39, No. 11, (2003), pp. 1492-1495.
Afon'kin et al., "Synthesis of Some Electron-Rich Aryl(hetaryl)oxiranes under Phase-Transfer and Homogeneous Conditions," Russian Journal of Organic Chemistry, vol. 44, No. 12, (2008), pp. 1776-1779.
Corey and Chaykovsky, "Dimethyloxosulfonium Methylide (($CH_3$)$_2$SOCH$_2$) and Dimethylsulfonium Methylide (($CH_3$)$_2$SCH$_2$). Formation and Application to Organic Synthesis," Journal of American Chemical Society, vol. 87, No. 5, (1965), pp. 1353-1364.
Mosset and Grée, "Trimethylsulfonium Methylsulfate, a Simple and Efficient Epoxidizing Agent," Synthetic Communications, vol. 15, No. 8, (1985), pp. 749-757.
Yu et al., "Synthesis and Fungicidal Evaluation of 2-Arylphenyl Ether-3-(1H-1,2,4-triazol-l-yl)propan-2-ol Derivatives," J. Agric. Food Chem., vol. 57, No. 11, (2009), pp. 4854-4860.
The Pesticide Manual, Fourteenth Edition, ed. C.D.S. Tomlin, British Crop Production Council, 2006, Entry 157—cinmethylin, pp. 195-196.
Uguina et al., "Alumina as Heterogeneous Catalyst for the Regioselective Epoxidation of Terpenic Diolefins with Hydrogen Peroxide," Journal of Molecular Catalysis A: Chemical, 2006, vol. 256, pp. 208-215.
Van Vliet et al., "Hexafluoroacetone in Hexafluoro-2-propanol: A Highly Active Medium for Epoxidation with Aqueous Hydrogen Peroxide," Synlett, No. 8, (2001), pp. 1305-1307.
Office Action, issued in co-pending U.S. Appl. No. 15/571,627, dated Mar. 19, 2018.
Final Office Action, issued in co-pending U.S. Appl. No. 15/571,627, dated Oct. 16, 2018.

\* cited by examiner

PROCESS FOR THE PREPARATION OF LIMONENE-4-OL

This application is a National Stage application of International Application No. PCT/EP2016/058963, filed Apr. 22, 2016. This application also claims priority under 35 U.S.C. § 119 to Indian Patent Application No. 1291/DEL/2015, filed May 8, 2015, and to European Application No. 15174608.8, filed Jun. 30, 2015.

This invention relates to a process for the preparation of limonene-4-ol of formula (II) by an epoxide ring opening isomerization of terpinolene epoxide of formula (I)

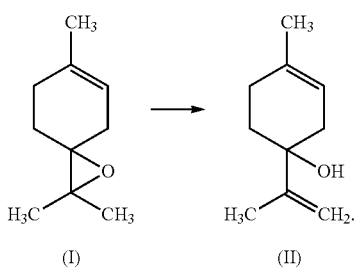

Limonene-4-ol is a valuable intermediate in the synthesis of terpinene-4-ol—an unsaturated tertiary terpene alcohol that occurs naturally in a number of essential oils. Terpinene-4-ol finds use as a component in synthetic essential oils which are compounded for use as flavors or perfumes. Because of high costs and uncertainty of supply of the natural product, synthetic routes to terpinene-4-ol have been developed, e.g. via epoxidation route that includes the step of epoxidation of terpinolene followed by the epoxide ring opening of the resulting terpinolene epoxide. Nevertheless, there is still room for improvement with regard to the step of the epoxide ring opening.

U.S. Pat. No. 3,676,504 describes a process for the preparation of limonene-4-ol from terpinolene epoxide, wherein the epoxide ring is opened by the reaction with an aqueous amine leading to N,N-dimethylaminohydrin. In the next step, N,N-dimethylaminohydrin is oxidized with hydrogen peroxide followed by pyrolysis of the resulting N-oxide giving limonene-4-ol in relatively low overall yield. The multistep route, low yield of the final product and long overall reaction time makes this process not suitable for an industrial scale preparation.

GB 1 307 053 describes a process for the preparation of limonene-4-ol by an epoxide ring opening isomerization of terpinolene epoxide in the presence of a p-toluene sulfonic acid as an isomerizing agent (catalyst). The reaction is carried out without a base. After the reaction is finished, a base is added in order to convert the p-toluene sulfonic acid into a salt. This process, however, suffers from relatively long reaction times.

Gurudutt K N et al. "Acid-catalyzed Rearrangement of Terpinolene Oxide", Indian Journal of Chemistry, Vol. 24B, August 1985, pages 820-823 describes the preparation of limonene-4-ol from terpinolene oxide with para-toluene sulphonic acid in the absence of a base.

It was accordingly an object of the present invention to provide an industrially simple process for the preparation of limonene-4-ol in good yields. Another object of the present invention was to reduce the reaction time.

Surprisingly we have found that these and further objects are, in part or in whole, achieved by the process of the present invention wherein terpinolene epoxide is subjected to an epoxide ring opening isomerization in the presence of a sulfonic acid and an organic base as a catalyst.

Accordingly, said process for the preparation of limonene-4-ol is a subject matter of the present invention.

The process according to the present invention entails a series of advantages and overcomes drawbacks of the prior art processes. It is a simple one-step synthesis leading to limonene-4-ol in very good yields. The reaction time is short and the process provides for a very good regioselectivity. Undesired side reactions leading to unwanted by-products are minimized. Sometimes, the product can be employed in the next reaction step without purification. These advantages make the process industrially simple and environmentally friendly.

Further embodiments of the invention are evident from the claims, the description and the examples. It is to be understood that the single features of the subject matter of the invention described herein can be applied not only in the combination given in each particular case but also in other combinations, without leaving the scope of the invention.

The ring opening isomerization according to the present invention is carried out in the presence of a sulfonic acid and an organic base as a catalyst.

The term "sulfonic acid" as used herein refers to a compound having an —SO$_3$H group bonded to a carbon atom.

Preferably, the sulfonic acid according to the present invention is selected from ($C_1$-$C_{14}$)-alkylsulfonic acids, halo-($C_1$-$C_6$)-alkylsulfonic acids, ($C_1$-$C_6$)-alkyl-($C_6$-$C_{10}$)-arylsulfonic acids, camphorsulfonic acid and any mixture thereof.

In a preferred embodiment of the present invention, the sulfonic acid is selected from ($C_1$-$C_{14}$)-alkylsulfonic acids, preferably from ($C_1$-$C_6$)-alkylsulfonic acids, most preferably from ($C_1$-$C_4$)-alkylsulfonic acids. Suitable examples are methane sulfonic acid, dodecyl sulfonic acid and the like. Preference is given to methane sulfonic acid.

In another equally preferred embodiment of the present invention, the sulfonic acid is selected from halo-($C_1$-$C_6$)-alkylsulfonic acids, preferably from halo-($C_1$-$C_4$)-alkylsulfonic acids. Suitable example is trifluoromethane sulfonic acid and the like.

In another equally preferred embodiment of the present invention, the sulfonic acid is selected from ($C_1$-$C_6$)-alkyl-($C_6$-$C_{10}$)-arylsulfonic acids, preferably from ($C_1$-$C_4$)-alkyl-phenylsulfonic acids. Suitable examples are p-toluene sulfonic acid and 2-naphthalene sulfonic acid. Preference is given to p-toluene sulfonic acid.

In yet another equally preferred embodiment of the present invention, the sulfonic acid is camphorsulfonic acid.

Alkyl chains of the alkyl radicals can be straight or branched. The prefix $C_n$-$C_m$ denotes in each case the possible number of carbon atoms in the group.

Examples of such radicals are:
$C_1$-$C_4$-alkyl: for example methyl, ethyl, n-propyl, isopropyl, n-butyl, 2-butyl (sec-butyl), iso-butyl, tert-butyl;
$C_1$-$C_6$-alkyl: $C_1$-$C_4$-alkyl as mentioned above, and also, for example, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, 2-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl; preferably methyl, ethyl, n-propyl, i-propyl, n-butyl and the like;

$C_1$-$C_{14}$-alkyl: $C_1$-$C_4$-alkyl as mentioned above, and also, for example, heptyl, octyl, nonyl, decyl, undecyl, dodecyl, tridecyl, tetradecyl, 6-methylheptyl, 7-methyloctyl, 8-methylnonyl, 9-methyldecyl, 10-methylundecyl, 11-methyldodecyl, 12-methyltridecyl, 13-methyltetradecyl and the like.

$C_1$-$C_4$-haloalkyl: $C_1$-$C_4$-alkyl as mentioned above which are partially or fully substituted by fluorine, chlorine, bromine and/or iodine, for example, chloromethyl, di-chloromethyl, trichloromethyl, fluoromethyl, difluoromethyl, trifluoromethyl, chloro-fluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3 trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl, 1-trifluoromethyl-1,2,2,2-tetrafluoroethyl and the like;

$C_1$-$C_6$-haloalkyl: $C_1$-$C_4$-haloalkyl and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl, dodecafluorohexyl and the like;

$C_6$-$C_{10}$-aryl: aromatic mono- or bi-cyclic ring having 6 to 10 carbon atoms, for example phenyl, naphthyl and the like;

The term "halogen" as used herein refers to fluorine, chlorine, bromine or iodine. Particular preference is given to fluorine and chlorine. Halogenated radical can be partially or fully halogenated, i.e. 1, 2, 3, 4 or 5 or all of the hydrogen atoms of a given radical can be replaced by a halogen atom. A partially or fully halogenated radical is termed below also "halo-radical". For example, partially or fully halogenated alkyl is termed as "haloalkyl".

Preferably, the sulfonic acid of the present invention is selected from methane sulfonic acid, dodecyl sulfonic acid, trifluoromethane sulfonic acid, p-toluene sulfonic acid, 2-naphthalene sulfonic acid, camphorsulfonic acid and any mixture thereof.

More preferably, the sulfonic acid of the present invention is selected from methane sulfonic acid, dodecyl sulfonic acid, p-toluene sulfonic acid, camphorsulfonic acid and any mixture thereof.

Most preferably, the sulfonic acid of the present invention is selected from methane sulfonic acid, p-toluene sulfonic acid and any mixture thereof.

The molar ratio of the sulfonic acid used as the catalyst to terpinolene epoxide can vary and is generally from 0.01:1 to 0.5:1, preferably from 0.02:1 to 0.4:1, more preferably from 0.03:1 to 0.3:1 and most preferably from 0.04:1 to 0.2:1.

The base according to the present invention is preferably selected from tertiary amines, pyridine, substituted pyridines, bicyclic amines and any mixture thereof.

In a preferred embodiment of the present invention, the base is selected from tertiary amines. Examples of suitable tertiary amines are tri-($C_1$-$C_6$)-alkylamines such as trimethylamine, triethylamine, tributylamine and N,N-diisopropylethylamine; di-($C_1$-$C_6$)-alkyl-phenylamines such as N,N-dimethylaniline and N,N-diethylaniline; N-methyl imidazole, N,N-dimethylaminopyridine and the like. Preference is given to triethylamine and N,N-dimethylaminopyridine. Particular preference is given to triethylamine.

In another equally preferred embodiment of the present invention, the base is selected from pyridine and substituted pyridines. Examples of suitable substituted pyridines are collidine, lutidine, picoline, N,N-dimethylaminopyridine and the like. Preference is given to pyridine and N,N-dimethylaminopyridine. Particular preference is given to N,N-dimethylaminopyridine.

In another equally preferred embodiment of the present invention, the base is selected from bicyclic amines. Examples of suitable bicyclic amines are 1,8-diazabicyclo[5.4.0]undec-7-en, 1,5-diazabicyclo[4.3.0]non-5-ene, 1,4-diazabicyclo[2.2.2]octane and the like.

Preferably, the base of the present invention the is selected from tri-($C_1$-$C_6$)-alkylamines such as trimethylamine, triethylamine, tributylamine and N,N-diisopropylethylamine; di-($C_1$-$C_6$)-alkyl-phenylamines such as N,N-dimethylaniline and N,N-diethylaniline; N-methyl imidazole, pyridine, collidine, lutidine, picoline, N,N-dimethylaminopyridine, 1,8-diazabicyclo[5.4.0]undec-7-en, 1,5-diazabicyclo[4.3.0]non-5-ene, 1,4-diazabicyclo[2.2.2]octane and any mixture thereof.

More preferably, the base of the present invention the is selected from tri-($C_1$-$C_6$)-alkylamines such as trimethylamine, triethylamine, tributylamine and N,N-diisopropylethylamine; di-($C_1$-$C_6$)-alkyl-phenylamines such as N,N-dimethylaniline and N,N-diethylaniline; N-methyl imidazole, pyridine, collidine, lutidine, picoline, N,N-dimethylaminopyridine, and any mixture thereof.

Most preferably, the base of the present invention is selected from tri-($C_1$-$C_6$)-alkylamines such as trimethylamine, triethylamine, tributylamine and N,N-diisopropylethylamine; pyridine, collidine, lutidine, picoline, N,N-dimethylaminopyridine, and any mixture thereof.

Particularly preferred base is selected from trimethylamine and N,N-dimethylaminopyridine.

In one preferred embodiment of the present invention, the base is used in the form of a free base. In this case said the base may form a salt with the sulfonic acid used as a catalyst after both of them are added to the reaction mixture.

In another preferred embodiment of the present invention, the base is used in the form of a salt with a sulfonic acid that may be the same or different to the sulfonic acid used as the catalyst. Preference is given to salts of the base with methanesulfonic acid or p-toluene sulfonic acid.

The sulfonic acid is usually used in excess with respect to the base. The molar ratio of the sulfonic acid used as the catalyst to the organic base calculated as a free base can vary and is generally from 4:1 to 1.01:1, preferably from 3:1 to 1.05:1, more preferably from 2.5:1 to 1.1:1 and most preferably from 1.8:1 to 1.2:1.

The epoxide ring opening isomerization according to the present invention is preferably carried out in an inert organic solvent.

The solvent is preferably selected from aliphatic hydrocarbons, halogenated aliphatic hydrocarbons, aromatic hydrocarbons, halogenated aromatic hydrocarbons, carboxylic acid esters, ethers, ketones or nitriles.

Suitable aliphatic hydrocarbons contain 5 to 10 carbon atoms, for example, n-pentane, n-hexane, n-heptane, n-octane, n-nonane, n-decane and their isomers, petroleum ethers, cyclohexane, methylcyclohexane, any mixture thereof and the like.

Examples of suitable halogenated aliphatic hydrocarbons, are methylene chloride, chloroform, 1,2-dichloroethane, any mixture thereof and the like.

Examples of suitable aromatic hydrocarbons are benzene, toluene, ethylbenzene, cymene, xylenes, mesitylene, any mixture thereof and the like.

Examples of suitable halogenated aromatic hydrocarbons are chlorobenzene, dichlorobenzene, any mixture thereof and the like.

Examples of suitable carboxylic acid ethers are ethyl acetate and the like.

Examples of suitable ethers are dioxane, anisole, tetrahydrofurane, methyltetrahydrofurane, methyl-tert-butylether, cyclopentylmethylether, any mixture thereof and the like.

Examples of suitable ketones are acetone, methyl ethyl ketone, diethyl ketone, t-butyl methyl ketone, methylisopropylketone, any mixture thereof and the like.

Examples of suitable ketones are acetonitrile, propionitrile, any mixture thereof and the like.

In one embodiment of the present invention, terpinolene epoxide and the solvent are pre-charged in the reaction vessel and then the sulfonic acid and the base are added.

In another embodiment of the present invention the sulfonic acid, the base and the solvent are pre-charged in the reaction vessel and then terpinolene epoxide is added.

The process according to the present invention can be carried out under atmospheric pressure or under slightly elevated or reduced pressure. Typically, the atmospheric pressure is employed.

The ring opening isomerization according to the present invention is usually effected at −10 to 60° C., preferably at 0 to 40° C. and more preferably at 10 to 30° C.

The starting materials according to the present invention are known compounds that are commercially available or can be prepared in a known manner.

Terpinolene epoxide of formula (I) can be prepared, for example, as described in U.S. Pat. No. 3,676,504.

Limonene-4-ol may be further subjected to a conventional hydrogenation to give terpinene-4-ol, as described, for example in GB 1 307 053.

Terpinene-4-ol can in turn be used as a starting material for the synthesis of oxabicycloalkane herbicides, in particular of (±)-2-exo-(2-Methylbenzyloxy)-1-methyl-4-isopropyl-7-oxabicyclo[2.2.1]heptane as described, for example in U.S. Pat. Nos. 4,487,945 or 4,542,244.

(±)-2-exo-(2-Methylbenzyloxy)-1-methyl-4-isopropyl-7-oxabicyclo[2.2.1]heptane (herein also referred to as the "exo-(±)-isomers", CAS RN 87818-31-3)

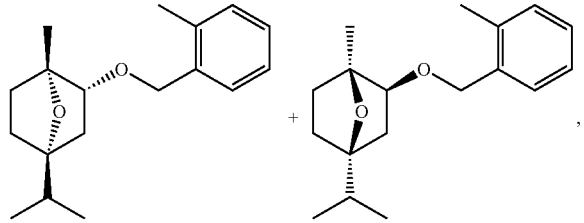

is the racemic mixture containing equal parts of the two enantiomers (+)-2-exo-(2-Methylbenzyloxy)-1-methyl-4-isopropyl-7-oxabicyclo[2.2.1]heptane (herein also referred to as the "exo-(+)-isomer", CAS RN 87818-61-9) and (−)-2-exo-(2-Methylbenzyloxy)-1-methyl-4-isopropyl-7-oxabicyclo[2.2.1]heptane (herein also referred to as the "exo-(−)-isomer", CAS RN 87819-60-1). The exo-(±)-isomers, the exo-(+)-isomer and the exo-(−)-isomer including their preparation and herbicidal properties are disclosed in EP 0 081 893 A2 (see Examples 29, 34, 35 and 62). Further preparation methods of these compounds are described in U.S. Pat. No. 4,487,945 (see Embodiments 46 and 48). The racemic mixture (±)-2-exo-(2-Methylbenzyloxy)-1-methyl-4-isopropyl-7-oxabicyclo[2.2.1]heptane is also described in the The Pesticide Manual, Fourteenth Edition, Editor: C.D.S. Tomlin, British Crop Production Council, 2006, entry 157, pages 195-196 with its common name cinmethylin, its IUPAC name (1RS,2SR,4SR)-1,4-epoxy-p-menth-2-yl 2-methylbenzyl ether and its Chemical Abstracts name exo-(±)-1-methyl-4-(1-methylethyl)-2-[(2-methylphenyl) methoxy]-7-oxabicyclo[2.2.1]heptane.

Limonene-4-ol and terpinene-4-ol are valuable intermediates in the preparation of (±)-2-exo-(2-Methylbenzyloxy)-1-methyl-4-isopropyl-7-oxabicyclo[2.2.1]heptane, any of its individual enantiomers or any non-racemic mixture thereof.

Limonene-4-ol and terpinene-4-ol may be further converted into (±)-2-exo-(2-Methylbenzyloxy)-1-methyl-4-isopropyl-7-oxabicyclo[2.2.1]heptane, any of its individual enantiomers or any non-racemic mixture thereof. Further conversion into (±)-2-exo-(2-Methylbenzyloxy)-1-methyl-4-isopropyl-7-oxabicyclo[2.2.1]heptane, any of its individual enantiomers or any non-racemic mixture thereof can be accomplished by methods known in the art such as, for example, those described in EP 0 081 893 A2 and U.S. Pat. No. 4,487,945.

Thus, in a further aspect of the present invention, there is provided a process for preparing (±)-2-exo-(2-Methylbenzyloxy)-1-methyl-4-isopropyl-7-oxabicyclo[2.2.1]heptane, any of its individual enantiomers or any non-racemic mixture thereof comprising the steps of:

(i) preparing limonene-4-ol (preferably terpinene-4-ol) as described herein, and
(ii) converting limonene-4-ol (preferably terpinene-4-ol) into (±)-2-exo-(2-Methylbenzyloxy)-1-methyl-4-isopropyl-7-oxabicyclo[2.2.1]heptane, any of its individual enantiomers or any non-racemic mixture thereof.

The invention is illustrated by the following examples without being limited thereto or thereby.

EXAMPLE 1

Isomerization with Dimethylaminopyridinium Mesylate (DMAP Mesylate) and Methanesulfonic Acid as Catalysts.

2 g (0.012 mol) terpinolene epoxide and 80 g (0.94 mol) dichloromethane were charged into the reaction vessel. 0.26 g (0.0012 mol) DMAP mesylate and 0.06 g (0.0006 mol) methanesulfonic acid were added. The mixture was stirred for 3 h at 25° C. Then, 50 ml water was added and the mixture was stirred for 2 minutes. Phases were separated and the organic phase was washed with 50 ml saturated aqueous NaCl-solution. After drying with sodium sulfate the solvent was distilled off at reduced pressure. The distillation residue contained 57% of limonene-4-ol, which corresponds to a yield of 63%.

EXAMPLE 2

Isomerization with Triethylammonium Mesylate and Methanesulfonic Acid as Catalysts 10 g (0.06 mol) terpinolene epoxide and 200 g (2.36 mol) dichloromethane were charged into the reaction vessel. 1.2 g (0.006 mol) triethylammonium mesylate and 0.3 g (0.003 mol) methanesulfonic acid were added. The mixture was stirred for 3 h at room temperature. Then 50 ml water was added and the mixture was stirred for 2 minutes. Phases were separated and the organic phase was washed with 50 ml saturated aqueous NaCl-solution. After drying with sodium sulfate the solvent was distilled off at reduced pressure. The distillation residue contained 61% of limonene-4-ol, which corresponds to a yield of 62.5%.

EXAMPLE 3

Isomerization with 4-Dimethylaminopyridine and Methanesulfonic Acid as Catalysts 1.1 g (0.009 mol) 4-dimethylaminopyridine and 357 g dichloromethane were charged into the reaction vessel. 1.3 g (0.014 mol) methanesulfonic acid was added. The mixture was stirred for 30 minutes. Then 250 g dichloromethane and 15 g (0.09 mol) terpinolene epoxide were added. The mixture was stirred for 4.5 h at room temperature. The dichloromethane solution was washed with 200 ml water and then with 200 ml saturated aqueous NaCl-solution. After drying with sodium sulfate the solvent was distilled off at reduced pressure. The distillation residue contained 58% of limonene-4-ol, which corresponds to a yield of 62%.

EXAMPLE 4

Isomerization with Dimethylaminopyridinium Tosylate (DMAP Tosylate) and Methanesulfonic Acid as Catalysts 2 g (0.012 mol) terpinolene epoxide and 80 g (0.94 mol) dichloromethane were charged into the reaction vessel. 0.38 g (0.0012 mol) DMAP tosylate and 0.06 g (0.0006 mol) methanesulfonic acid were added. The mixture was stirred for 6 h at room temperature. Then 50 ml water was added and the mixture was stirred for 2 minutes. Phases were separated and the organic phase was washed with 30 ml saturated aqueous NaCl-solution. After drying with sodium sulfate the solvent was distilled off at reduced pressure. The distillation residue contained 56% of limonene-4-ol, which corresponds to a yield of 59%.

COMPARATIVE EXAMPLE 1

Isomerization in Toluene/Acetone with P-Toluenesulfonic Acid as Catalyst 50 g (0.30 mol) terpinolene epoxide (92.2%) and 217.5 g (2.36 mol) toluene were charged into the reaction vessel. A solution of 1 g (0.005 mol) p-toluenesulfonic acid (monohydrate) in 13.2 g (0.23 mol) acetone was added. The mixture was stirred for 47 h at room temperature. 36 g sodium bicarbonate solution (5%) was added and the mixture was stirred for 45 minutes. Water was removed by azeotropic distillation. Precipitated salt was filtered off and washed with toluene. Filtrate and wash toluene were combined and toluene was distilled off with a 30 cm column. The distillation residue contained 51% of limonene-4-ol, which corresponds to a yield of 58%.

EXAMPLE 5

Isomerization in Acetone (Dried) with Triethylammonium Tosylate and P-Toluenesulfonic Acid as Catalysts 3.2 g (20 mmol) terpinolene epoxide (95%) and 30 mL (23.7 g) acetone (dried) were charged into the reaction vessel. The mixture was cooled to 5-10° C. and treated with 170 mg (1 mmol) of p-toluenesulfonic acid and 274 mg (1 mmol) of triethylammonium tosylate. The mixture was stirred for 1 h at room temperature (25° C.). The mixture was extracted with methyl tert-butyl ether and water, washed with sodium bicarbonate solution, dried and evaporated. The residue contained 45% of limonene-4-ol (quantified), which corresponds to a yield of 51%.

COMPARATIVE EXAMPLE 2

Isomerization in Acetone (Dried) with P-Toluenesulfonic Acid as Catalyst 3.2 g (20 mmol) terpinolene epoxide (95%) and 30 mL (23.7 g) acetone (dried) were charged into the reaction vessel. The mixture was cooled to 5-10° C. and treated with 170 mg (1 mmol) of p-toluenesulfonic acid. The mixture was stirred for 1 h at room temperature (25° C.). The mixture was extracted with methyl tert-butyl ether and water, washed with sodium bicarbonate solution, dried and evaporated. The residue contained 38% of limonene-4-ol (quantified), which corresponds to a yield of 43%.

EXAMPLE 6

Isomerization in Acetone (Not Dried) with Triethylammonium Tosylate and P-Toluenesulfonic Acid as Catalysts 3.2 g (20 mmol) terpinolene epoxide (95%) and 30 mL (23.7 g) acetone (not dried) were charged into the reaction vessel. The mixture was cooled to 5-10° C. and treated with 170 mg (1 mmol) of p-toluenesulfonic acid and 274 mg (1 mmol) of triethylammonium tosylate. The mixture was stirred for 1 h at room temperature (25° C.). The mixture was extracted with methyl tert-butyl ether and water, washed with sodium bicarbonate solution, dried and evaporated. The residue contained 26.2% of limonene-4-ol (quantified), which corresponds to a yield of 28.4%.

COMPARATIVE EXAMPLE 3

Isomerization in Acetone (Not Dried) with P-Toluenesulfonic Acid as Catalyst 3.2 g (20 mmol) terpinolene epoxide (95%) and 30 mL (23.7 g) acetone (not dried) were charged into the reaction vessel. The mixture was cooled to 5-10° C. and treated with 170 mg (1 mmol) of p-toluenesulfonic acid. The mixture was stirred for 1 h at room temperature (25° C.). The mixture was extracted with methyl tert-butyl ether and water, washed with sodium bicarbonate solution, dried and evaporated. The residue contained 13.3% of limonene-4-ol (quantified), which corresponds to a yield of 14.4%.

The invention claimed is:
1. A process for the preparation of limonene-4-ol of formula (II)

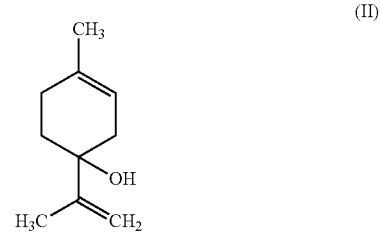

comprising subjecting a selective epoxide ring opening isomerization to a terpinolene epoxide of formula (I)

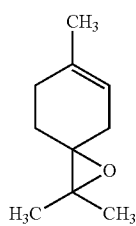

(I)

in the presence of a sulfonic acid and an organic base as a catalyst.

2. The process of claim 1, wherein the sulfonic acid is selected from the group consisting of ($C_1$-$C_{14}$)-alkylsulfonic acids, halo-($C_1$-$C_6$)-alkylsulfonic acids, ($C_1$-$C_6$)-alkyl-($C_6$-$C_{10}$)-arylsulfonic acids, camphorsulfonic acid and any mixture thereof.

3. The process of claim 1, wherein the sulfonic acid is selected from the group consisting of methane sulfonic acid, dodecyl sulfonic acid, trifluoromethane sulfonic acid, p-toluene sulfonic acid, 2-naphthalene sulfonic acid, camphorsulfonic acid and any mixture thereof.

4. The process of claim 1, wherein the base is selected from the group consisting of tertiary amines, pyridine, substituted pyridines, bicyclic amines and any mixture thereof.

5. The process of claim 1, wherein the base is selected from the group consisting of trimethylamine, triethylamine, tributylamine, N,N-diisopropylethylamine, N,N-dimethylaniline, N,N-diethylaniline, N-methyl imidazole, pyridine, collidine, lutidine, picoline, N,N-dimethylaminopyridine, 1,8-diazabicyclo[5.4.0]undec-7-en, 1,5-diazabicyclo[4.3.0]non-5-ene and 1,4-diazabicyclo[2.2.2]octan.

6. The process of claim 1, wherein the base is selected from the group consisting of triethylamine and N,N-dimethylaminopyridine.

7. The process of claim 1, wherein the base is used in the form of a free base or in the form of a salt with a sulfonic acid that may be the same or different to the sulfonic acid used as the catalyst.

8. The process of claim 7, wherein the base is used in the form of a salt with methanesulfonic acid or p-toluene sulfonic acid.

9. The process of claim 1, wherein the molar ratio of the sulfonic acid used as the catalyst to terpinolene epoxide is from 0.01:1 to 0.5:1.

10. The process of claim 1, wherein the molar ratio of the sulfonic acid used as the catalyst to the organic base calculated as a free base is from 4:1 to 1.01:1.

11. The process of claim 1, wherein the isomerization is carried out in an inert organic solvent.

12. The process of claim 11, wherein the solvent is selected from the group consisting of aliphatic hydrocarbons, halogenated aliphatic hydrocarbons, aromatic hydrocarbons, halogenated aromatic hydrocarbons, carboxylic acid esters, ethers, ketones and nitriles.

13. The process of claim 1, wherein the isomerization is carried out at −10 to 60° C.

14. The process of claim 1, wherein limonene-4-ol is further reduced to give terpinene-4-ol.

15. The process of claim 1, wherein terpinolene epoxide of formula (I) is prepared via epoxidation of terpinolene.

16. A process for preparing (±)-2-exo-(2-Methylbenzyloxy)-1-methyl-4-isopropyl-7-oxabicyclo[2.2.1]heptane, any of its individual enantiomers or any non-racemic mixture thereof, comprising preparing limonene-4-ol of formula (II) in accordance with claim 1.

17. The process of claim 16, further comprising hydrogenating limonene-4-ol to afford terpinene-4-ol.

18. The process of claim 17, further comprising treating terpinene-4-ol successively or concurrently with an oxidizing agent and an acid in an inert solvent to effect epoxidation and cyclization to give (±)-2-exo-hydroxy-1-methyl-4-isopropyl-7-oxabicyclo[2.2.1]heptane.

19. The process of claim 18, further comprising reacting (±)-2-exo-hydroxy-1-methyl-4-isopropyl-7-oxabicyclo[2.2.1]heptane with a compound of the formula WCH$_2$L wherein W is 2-methylphenyl and L is a leaving group to afford (±)-2-exo-(2-Methylbenzyloxy)-1-methyl-4-isopropyl-7-oxabicyclo[2.2.1]heptane, any of its individual enantiomers or any non-racemic mixture thereof.

* * * * *